(12) United States Patent
Endo et al.

(10) Patent No.: US 7,138,239 B2
(45) Date of Patent: Nov. 21, 2006

(54) METHOD AND REAGENT FOR TESTING FOR MULTIPLE ORGAN FAILURE IN SIRS BY CYTOCHROME C MEASUREMENT

(75) Inventors: Fumio Endo, Kumamoto (JP); Naoto Adachi, Kumamoto (JP); Hiroyuki Nunoi, Miyazaki (JP); Keisuke Watanabe, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 698 days.

(21) Appl. No.: 10/139,933

(22) Filed: May 6, 2002

(65) Prior Publication Data

US 2002/0192712 A1 Dec. 19, 2002

(30) Foreign Application Priority Data

May 9, 2001 (JP) ............................. 2001-138369

(51) Int. Cl.
    *G01N 33/53* (2006.01)
(52) U.S. Cl. .................. 435/7.1; 435/7.92; 435/7.93; 435/7.94; 436/501; 436/518; 436/811
(58) Field of Classification Search .................. 435/6, 435/7.1, 7.92–7.94, 975; 436/501, 518, 811, 436/808, 524, 528
See application file for complete search history.

(56) References Cited

U.S. PATENT DOCUMENTS

| | | | | |
|---|---|---|---|---|
| 4,444,879 | A * | 4/1984 | Foster et al. | 435/7.95 |
| 5,780,237 | A | 7/1998 | Bursten et al. | |
| 6,670,138 | B1 * | 12/2003 | Gonzalez-Zulueta et al. | 435/7.1 |
| 2002/0137106 | A1 * | 9/2002 | Leung et al. | 435/7.9 |
| 2002/0188104 | A1 * | 12/2002 | Kornbluth et al. | 530/350 |
| 2004/0146892 | A1 * | 7/2004 | Murphy et al. | 435/6 |

FOREIGN PATENT DOCUMENTS

| | | |
|---|---|---|
| DE | 41073334 A1 | 9/1991 |
| GB | 2241782 A | 9/1991 |
| JP | H03-257367 | 11/1991 |
| WO | WO98/02579 | 1/1998 |

OTHER PUBLICATIONS

Voller, The Enzyme Linked Immunosorbent Assay (ELISA), Diagnostic Horizons, vol. 2, No. 1, Feb. 1978.*

Jemmerson et al., Preparation of Site-Specific Anti-Cytochrome c Antibodies and Their Application, Methods in Enzymology, vol. 74, pp. 244-262, 1981.*

Japanese laid-open Publication No. 3-257367 with English abstract (application No. 02-057236, filed Aug. 3, 1990).

M. Fujimura, et al. "Cytosolic Redistribution of Cytochrome c After Transient Focal Cerebral Ischemia in Rats," *Journal of Cerebral Blood Flow and Metabolism*, vol. 18, No. 11, pp. 1239-1247, 1998.

Related pending U.S. Appl. No. 10/129,644, filed May 6, 2002, entitled "Method and Reagent for Detecting Cell Death".

Dinsdale, et al., "Redistribution of Cytochrome *c* Precedes the Caspase-Dependent Formation of Ultracondensed Mitochondria, with a Reduced Inner Membrane Potential, in Apoptotic Monocytes", *American Journal of Pathology*, 155(2): 607-618, 1999.

European Search Report for related EP application No. 02253172.7.

Antonawich, "Translocation of Cytochrome C Following Transient Global Ischemia in the Gerbil", Neuroscience Letters (1999), v. 274, No. 2, pp. 123-126.

Hetts, "To Die or No to Die: An Overview of Apoptosis and its Role in Disease", JAMA: The Journal of American Medical Association (1998), v. 279, No. 4, pp. 300-307.

Jemmerson, et al., "A Monoclonal Antibody Specific for a Cytochrome C T Cell Stimulatory Peptide Inhibits T Cell Responses and Affects the way the Peptide Associates with Antigen-Presenting Cells", European Journal of Immunology (1991), v. 21, No. 1, pp. 143-151.

Los, et al., "Cytochrome *C* is Rapidly Released from the Cell Upon Apoptosis Induction: A New Marker for Cell Death *in vivo*", Immunology Letters (2000), v. 73, No. 2-3, p. 239.

Shounan, et al., "Apoptosis Detection by Annexin V Binding: A Novel Method for the Quantitation of Cell-Mediated Cytotoxicity", Journal of Immunological Methods (1998), v. 217 No. 1-2, pp. 61-70.

Ushmorov, et al., "Nitric Oxide-Induced Apoptosis in Human Leukemic Lines Requires Mitochrondrial Lipid Degradation and Cytochrome C Release", Blood (1999), v. 93, No. 7, pp. 2342-2352.

Supplemental European Search Report (EP 00 97 4820).

* cited by examiner

*Primary Examiner*—Long V. Le
*Assistant Examiner*—Gary W. Counts
(74) *Attorney, Agent, or Firm*—Brenda Herschbach Jarrell; Choate, Hall and Stewart, LLP

(57) ABSTRACT

A method for testing for multiple organ failure in SIRS, which comprises determining cytochrome C in body fluid and using the determined result as an index of the multiple organ failure, and a reagent for testing for multiple organ failure in SIRS, which comprises a reagent for determination of cytochrome C in body fluid.

2 Claims, 1 Drawing Sheet

METHOD AND REAGENT FOR TESTING FOR MULTIPLE ORGAN FAILURE IN SIRS BY CYTOCHROME C MEASUREMENT

This application claims the priority of Japanese Patent Application No. 2001-138369, filed May 9, 2001.

BACKGROUND OF THE INVENTION

The present invention relates to a method and a reagent for testing multiple organ failure in systemic inflammatory response syndrome (SIRS).

SIRS is a syndrome in which the immune system is nonspecifically activated without a specific target in response to invasion to a living body and thus control of cytokine production becomes impossible to cause severe multiple organ failure, in contrast to systemic lupus erythematosus (SLE) and graft versus host disease (GVHD) in which cytokine levels increase in response to a specific antigen (an autoantigen such as double strand DNA in SLE and an alloantigen in GVHD) to cause inflammation (Bone RC, Crit Care Med 24: 1125–1128, 1996; Davies M G. Et al., Br J Surgery 84: 920–935, 1997).

SIRS includes hemophagocytic syndrome (HPS), septicemia, severe pancreatitis such as acute pancreatitis, postoperative organ disorder, is observed in ICU patients in most cases, and is a syndrome of which prognosis is difficult.

As for an index of multiple organ failure, judgment has been made by scoring physical signs such as body temperature, respiratory frequence, blood gas and heart rate. However, the judgment is considered to be poor in objectivity.

SUMMARY OF THE INVENTION

An object of the present invention is to provide a method and a reagent for testing for multiple organ failure in SIRS, which are simple and show superior sensitivity and quantitation performance.

Cytochrome C is known as an important protein in the electron transport system in mitochondria. It is reported that, when a cell is exposed to a stimulus that triggers apoptosis and enters into an apoptosis state, cytochrome C in the mitochondria is rapidly released into cytosol (Dinsdale, D. et al., American J. Pathol. 155: 607–18, 1999). It is also reported that cytochrome C in the cytosol is associated with activation of caspase-3, which is a key factor of apoptosis, and an increase of cytochrome C is involved in the progress of apoptosis (Medina, V. et al., Cancer Research, 57: 3697–707, 1999).

The inventors of the present invention considered that, when apoptosis occurred in a living body, cytochrome C released from mitochondria could also be measured in blood. Then, they established an ELISA method for measuring cytochrome C, and found that the cytochrome C level in blood strongly correlated with a score of multiple organ failure. Thus, they accomplished the present invention.

The present invention provides a method for testing for multiple organ failure in SIRS by determining cytochrome C in body fluid, and a method and a reagent that can be used in such a method. In particular, it provides the followings.

(1) A method for testing for multiple organ failure in SIRS, which comprises determining cytochrome C in body fluid and using the determined result as an index of the multiple organ failure.

(2) The method according to (1), wherein cytochrome C is determined by an immunochemical method.

(3) A reagent for testing for multiple organ failure in SIRS, which comprises a reagent for determination of cytochrome C in body fluid.

(4) The reagent according to (3), wherein cytochrome C is determined by an immunochemical method.

The present inventors have revealed that the determination of cytochrome C is useful for test and prognosis of multiple organ failure in SIRS. Therefore, the present invention provides a method and a reagent for testing for multiple organ failure in SIRS, which are simple and show superior sensitivity and quantitation performance.

DETAILED DESCRIPTION OF THE INVENTION

Figure 1:
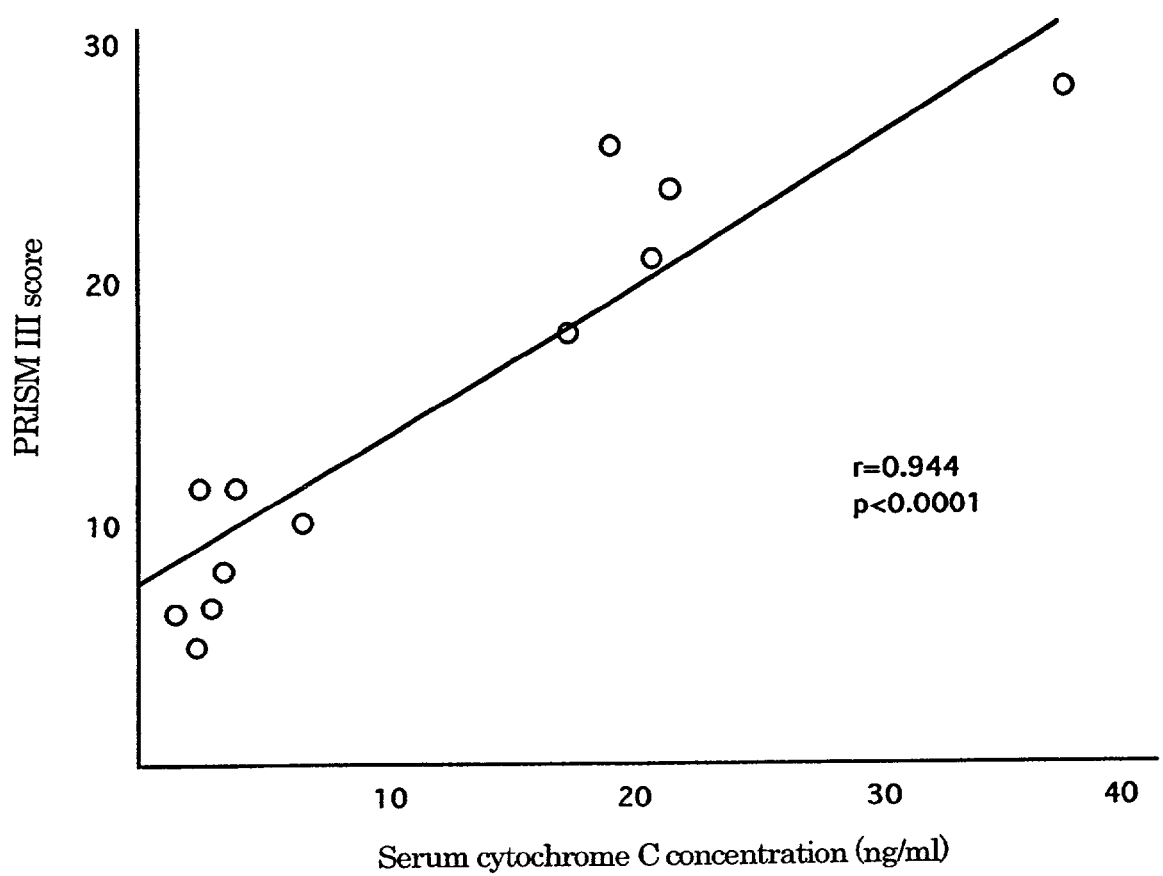
FIG. 1 shows correlation of determined values of cytochrome C in sera of SIRS patients with a multiple organ failure score.

Hereafter, embodiments of the present invention will be explained in detail.

The test method of the present invention is a method for testing for multiple organ failure in SIRS, which is characterized by determining cytochrome C in body fluid and using the determined result as an index of the multiple organ failure.

The body fluid refers to blood, plasma, serum, cerebrospinal fluid or the like collected from a living body.

As the method for measuring cytochrome C, there can be mentioned an immunochemical method, method utilizing electrophoresis, method utilizing chromatography and so forth. Examples of the methods utilizing electrophoresis include a method wherein polyacrylamide gel electrophoresis is performed to detect cytochrome C as a band, a method wherein capillary electrophoresis is performed to detect cytochrome C as a peak and so forth. Further, as the method utilizing chromatography, a method wherein high performance liquid chromatography is performed to detect cytochrome C as a peak and so forth can be mentioned. In order to increase sensitivity, fluorescence labeling may be used in some cases, but the present invention is not limited to such cases.

As the method for measuring cytochrome C, an immunochemical method is preferred in view of sensitivity and simplicity. The term "immunochemical method" used herein refers to a method of determining cytochrome C by using an antibody directed to cytochrome C. As the immunochemical method, there can be mentioned various methods such as a competitive method in which cytochrome C is labeled, a sandwich method in which an antibody is labeled, a latex bead method in which agglutination of antibody-coated beads is observed and so forth, and they are included in preferred embodiments of the present invention so long as an antibody directed to cytochrome C is used. The antibody may be a monoclonal or polyclonal antibody. As the labeling method, there can also be mentioned various methods such as labeling with a radioactive isotope, labeling with a compound showing electro-chemiluminescence, fluorescence labeling, labeling with an enzyme, labeling with biotin and so forth, but the present invention is not limited to these examples.

As an example of the immunochemical method for measuring cytochrome C, a sandwich method will be explained below step by step.

1) An antibody directed to cytochrome C is immobilized on beads or a cup. The beads may be microbeads. In this case, microbeads of magnetic substance are preferred. The immobilization may be achieved by a covalent or non-covalent bond. Usually, nonspecific binding sites on the beads or cup are blocked by using a protein such as bovine serum albumin (BSA) or casein or a surfactant such as Tween 20.
2) A specimen is diluted with a buffer containing a protein such as BSA or casein or a surfactant such as Tween 20, if required, and added to the beads or the cup. Further, a known amount of cytochrome C is similarly diluted and added.
3) The beads or the cup are/is washed with a buffer containing a surfactant such as Tween 20, if required, and a labeled antibody diluted with a buffer containing a protein such as BSA or casein or a surfactant such as Tween 20, if required, is added thereto.
4) The beads or the cup are/is washed with a buffer containing a surfactant such as Tween 20, if required, and measurement is performed by a method corresponding with the label. For example, radioactivity is measured when it is radioactively labeled, or enzymatic activity is measured when it is labeled with an enzyme. Further, when it is labeled with biotin, labeled avidin is further added and measurement is performed by a method corresponding with the label.
5) A calibration curve is created by using known amounts of cytochrome C, and the amount of cytochrome C contained in the specimen is calculated.

With the above steps, cytochrome C in the specimen is determined.

By using the determination result as an index, the test for multiple organ failure in SIRS is performed. For example, when the determined value of cytochrome C is higher than a normal value, it can be considered that multiple organ failure in SIRS is detected.

The present invention also relates to a reagent for testing for multiple organ failure in SIRS, which comprises a reagent for determination of cytochrome C in body fluid. The reagent for determination of cytochrome C is preferably one for determination by an immunochemical method. An example of the reagent is an antibody directed to cytochrome C.

The immunochemical method is preferably a sandwich method. The sandwich method is an immunochemical method such as ELISA utilizing an antigen sandwiched by an immobilized antibody and a labeled antibody. The sandwich method is a method suitable to determine cytochrome C in the body fluid containing a high concentration of protein with high sensitivity.

The test reagent of the present invention is preferably a test reagent used for measuring cytochrome C in body fluid by the sandwich method, which comprises an antibody directed to cytochrome C as an ingredient. This measurement reagent may have the same constitution as that of a reagent (kit) used in a usual sandwich method except that the anti-cytochrome C antibody is used as an antibody. For example, the reagent for measuring cytochrome C by the sandwich method may contain 1) an anti-cytochrome C antibody-coated solid phase such as an anti-cytochrome C antibody-coated cup or anti-cytochrome C antibody-coated beads, 2) a labeled anti-cytochrome C antibody, 3) a cytochrome C standard solution of a known concentration, 4) a diluent and 5) a washing solution. Further, if labeling with an enzyme is used, 6) a chromogenic substrate and 7) a solution for terminating a reaction may be included.

The cytochrome C concentration in body fluid correlates well with the PRISM III score which has been used as an index of multiple organ failure. Therefore, by measuring the cytochrome C concentration, it is possible to objectively judge multiple organ failure occurring in SIRS.

In particular, in case of serum, if the cytochrome C concentration exceeds 10 ng/ml, the course of the disease is poor. By measuring the cytochrome C concentration, prognosis becomes possible.

EXAMPLES

The present invention will be explained more specifically with reference to the following examples. However, the scope of the present invention is not limited to these examples. % refers to % by mass unless otherwise indicated.

Reference Example 1

Measurement of Cytochrome C by ELISA

Cytochrome C is measured by the following procedure.

1) Purification of Anti-Cytochrome C Antibody

A rabbit is immunized with rat cytochrome C (Sigma) to obtain antiserum directed to cytochrome C. To the antiserum, ammonium sulfate is added at a final concentration of 2 M, and it is stirred at room temperature (20–30° C.) for 5 hours. The stirred solution is centrifuged at 10000 rpm for 30 minutes and the supernatant is discarded. The precipitation is dissolved in 0.1 M phosphate buffer (pH 7.2) and dialyzed against the same buffer. The dialyzed solution is applied to a column of a carrier obtained by binding bovine cytochrome C to CNBr-Sepharose 4B (Pharmacia). The column is washed with 0.01 M Tris-HCl buffer (pH 7.5) containing 0.15 M NaCl, and then anti-cytochrome C antibodies are eluted with 0.1 M guanidine hydrochloride. The eluted solution is dialyzed against 0.01 M Tris-HCl buffer (pH 7.5) containing 0.15 M NaCl to obtain purified antibodies (IgG).

2) Preparation of Anti-Cytochrome C Antibody F(ab')$_2$

The purified IgG is dialyzed against 0.1 M acetate buffer (pH 4.2). To the dialyzed IgG solution, pepsin (Sigma) is added in a mass concentration ratio of 20:1 and it is allowed to react at 37° C. for 16 hours. The solution after the reaction is adjusted to pH 7.5 with 1 N NaOH and subjected to gel filtration by using a Sephacryl S-200 (Pharmacia) column equilibrated with 0.01 M Tris-HCl buffer (pH 7.5) containing 0.15 M NaCl. A first peak of the fractions obtained from the gel filtration is collected and concentrated to obtain an anti-cytochrome C antibody F(ab')$_2$ solution.

3) Preparation of Horseradish Peroxidase (HRP)-Labeled Anti-Cytochrome C Antibody F(ab')$_2$ To 1 ml of HRP (Toyobo) solution adjusted to 4 mg/ml, 60 μl of 0.1 M sodium metaperiodate is added, and it is stirred at room temperature (20–30° C.) for 20 minutes, and dialyzed against 0.001 M acetate buffer (pH 4.4). The dialyzed solution is adjusted to pH 9.0–9.5 with 0.2 M sodium carbonate solution. To this solution, 1 ml of the anti-cytochrome C antibody F(ab')$_2$ solution (4 mg/ml) dialyzed against 0.1 M carbonate buffer (pH 9.5) is added and it is stirred at room temperature (20–30° C.) for 2 hours. Then 50 μl of sodium borohydride solution adjusted to 4 mg/ml is added, and it is stirred at 4° C. for 2 hours and left standing for 16 hours. This solution is dialyzed against phosphate buffer (pH 7.2) containing 0.15 M NaCl and then subjected to gel filtration by using a Sephacryl S-200

(Pharmacia) column. A first peak of the fractions obtained from the gel filtration is collected and diluted with 0.2 M disodium phosphate buffer (pH 5.4) containing 25% rabbit serum (Nippon Seibutsu Zairyo) to obtain a HRP-labeled anti-cytochrome C antibody F(ab')$_2$ solution (labeled antibody solution).

4) Preparation of Anti-Cytochrome C Antibody-Immobilized Cup

The purified IgG obtained in 1) is adjusted to an absorbance of 0.1 with 0.01 M Tris-HCl buffer (pH 7.5). 100 µl of this antibody solution is introduced into a polystyrene cup, and allowed to react at 4° C. for 16 hours and the cup is washed three times (for 4 seconds each time) with 0.01 M Tris-HCl buffer (pH 7.5) containing 0.15 M NaCl and 0.01% Tween 20 by using a washer designed for use in EIA. 200 µl of 0.01 M Tris-HCl buffer (pH 7.5) containing 0.5% bovine albumin is added to the washed cup and allowed to react at 4° C. for 16 hours again to obtain an antibody-immobilized solid phase cup.

5) Preparation of Standard Antigen

Rat cytochrome C (Sigma) is diluted with 0.05 M Tris buffer (pH 7.5) containing 2% BSA, 0.01 M EDTA 2Na, 0.1% NaN$_3$, 0.01% Tween 20 and 0.15 M NaCl to prepare 50–0.05 ng/ml dilutions.

6) Measurement

The bovine albumin solution in the anti-cytochrome C antibody-immobilized cup is sucked out and 50 µl of 0.05 M Tris buffer (pH 7.5) containing 2% BSA, 0.01 M EDTA 2Na, 0.1% NaN$_3$, 0.01% Tween 20 and 0.15 M NaCl is introduced into the aforementioned cup. 50 µl each of diluted standard antigen solutions and a specimen is added to the cup and allowed to react at room temperature (20–30° C.) for 1 hour. After the reaction, the cup is washed three times (for 4 seconds each time) with 0.005 M Tris buffer (pH 7.5) containing 0.01% Tween 20, 0.0015 M NaCl, 0.0015% methyl paraoxybenzoate and 0.005% 2-chloroacetamide by using a washer designed for use in EIA. After the washing, 100 µl of the labeled antibody solution is added and allowed to react at room temperature (20–30° C.) for 1 hour. After the reaction, the cup is washed three times (for 4 seconds each time) with 0.005 M Tris buffer (pH 7.5) containing 0.01% Tween 20, 0.15 M NaCl, 0.0015% methyl paraoxybenzoate and 0.005% 2-chloroacetamide by using a washer designed for use in EIA. After the washing, 100 µl of 0.1 M citrate buffer (pH 4.2) containing 1.5 mg/ml ABTS (2,2-azino-bis-(3-ethylbenzothiazoline-6-sulfonic acid) is added and allowed to react at room temperature (20–30° C.) for 1 hour, and then 100 µl of 0.013% NaN$_3$ solution is added to terminate the reaction. The absorbance of the color-developed solution is measured at 405 nm by using a spectrophotometer.

7) Characteristics of Standard Antigen Curve

Absorbance value of a blank is subtracted from each of absorbance values of the cytochrome C at various concentrations and the specimen. The standard antigen concentration and the absorbance of the standard antigen are plotted on the horizontal axis and the vertical axis, respectively, to draw a standard curve. Based on the standard antigen curve, the amount of cytochrome C contained in the specimen is calculated.

Example 1

Quantitation of cytochrome C in sera of SIRS patients

Cytochrome C levels in sera of HPS, septicemia, ambustion, acute pancreatitis, postoperative patients who were SIRS patients, and normal subjects were measured by using the ELISA system for measuring cytochrome C described in Reference Example 1.

As a result, as shown in Table 1, 15 normal subjects were all negative (<0.05 ng/ml), whereas 13 out of 13 HPS patients were positive (100%), 8 out of 8 septicemia patients were positive (100%), 4 out of 6 ambustion patients were positive (67%), 9 out of 9 acute pancreatitis patients were positive (100%), and 6 out of 8 postoperative patients were positive (75%). Further, HPS patients having a high blood cytochrome C concentration tended to show poor course of the disease.

TABLE 1

Determined values of cytochrome C in sera of SIRS patients

| Disease | Serum cytochrome C concentration (ng/ml) | | | | |
|---|---|---|---|---|---|
| HSP | 38.0 | 22.0 | 19.0 | 18.8 | 16.5 |
|  | 7.2 | 4.3 | 3.6 | 2.9 | 2.7 |
|  | 2.1 | 1.2 | 1.1 |  |  |
| Septicemia | 7.6 | 19.0 | 17.0 | 5.4 | 17.0 |
|  | 16.0 | 18.0 | 11.0 |  |  |
| Ambustion | 0.39 | 1.2 | 0.6 | 2.5 | <0.05 |
|  | <0.05 |  |  |  |  |
| Acute pancreatitis | 36.0 | 175.0 | 58.0 | 30.0 | 14.0 |
|  | 16.5 | 170.0 | 420.0 | 13.5 |  |
| Postoperative | 0.23 | 7.0 | 0.24 | 3.1 | <0.05 |
|  | <0.05 | 0.18 | 0.3 |  |  |

*: All the 15 normal subjects had values less than the detection limit (<0.05 ng/ml).

Further, in HPS patients, 4 out of 5 patients whose serum cytochrome C concentration was not less than 10 ng/ml deceased (80%), while 8 patients whose serum cytochrome C concentration was less than 10 ng/ml did not deceased (100%). This shows that patients whose serum cytochrome C concentration is not less than 10 ng/ml are poor in the course of the disease.

Example 2

Correlation of Determined Values of Cytochrome C in Sera of SIRS Patients with a Multiple Organ Failure Score With respect to 12 SIRS patients, a multiple organ failure score, PRISM III was calculated according to Pollack M M et al. (Crit Care Med 24: 743–752, 1996), and correlation thereof with the serum cytochrome C concentration was investigated.

As a result, the cytochrome C concentration correlated well with the PRISM III score. This shows that the cytochrome C concentration is useful as an objective index of multiple organ index.

What is claimed is:

1. A method for testing for multiple organ failure in a patient with systemic inflammatory response syndrome, which comprises determining the level of cytochrome C in blood, plasma, serum or cerebrospinal fluid of said patient and comparing the determined level with a normal value to indicate multiple organ failure in said patient when the determined level of said cytochrome C is increased compared to said normal value.

2. The method according to claim 1, wherein the level of cytochrome C is determined by an immunochemical method.

* * * * *